United States Patent [19]

Swenton et al.

[11] Patent Number: 4,663,445

[45] Date of Patent: May 5, 1987

[54] 1-FLUORO, 4-FLUORO, AND 1,4-DIFLUORO-2'-HALO ANTHRACYCLINE ANTIBIOTICS

[75] Inventors: John S. Swenton; Derek Horton; Waldemar Priebe; Gary W. Morrow, all of Columbus, Ohio

[73] Assignee: The Ohio State Research Foundation, Columbus, Ohio

[21] Appl. No.: 714,148

[22] Filed: Mar. 20, 1985

[51] Int. Cl.⁴ ............................................. C07H 15/24
[52] U.S. Cl. ...................................... 536/6.4; 536/18.6
[58] Field of Search ............................ 536/6.4; 514/34

[56] References Cited

U.S. PATENT DOCUMENTS 4,125,607 11/1978 Arcamone et al. ................... 536/6.4
4,427,664 1/1984 Horton et al. ........................ 536/6.4
4,472,571 9/1984 Fujiwara et al. ..................... 536/6.4

Primary Examiner—Johnnie R. Brown
Assistant Examiner—Elli Peselel

Attorney, Agent, or Firm—Biebel, French & Nauman

[57] ABSTRACT

Anthracycline antibiotics represented by the formula (I)

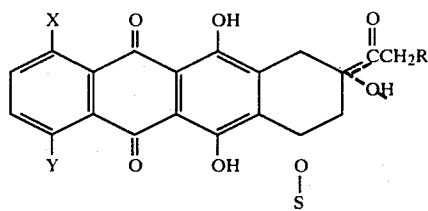

wherein R is hydrogen or hydroxyl, one of X and Y is fluorine and the other is hydrogen or both X and Y are fluorine, and S is a 2-halo sugar moiety; pharmaceutical preparations containing the same; and a method for inhibiting the growth of mammalian tumors are disclosed.

9 Claims, No Drawings

1-FLUORO, 4-FLUORO, AND 1,4-DIFLUORO-2'-HALO ANTHRACYCLINE ANTIBIOTICS

BACKGROUND OF THE INVENTION

Anthracycline antibiotics including doxorubicin, daunorubicin, and carminomycin are important chemotherapeutic agents in the treatment of a broad spectrum of neoplastic conditions including acute myeloblastic and lymphoblastic leukemias. Doxorubicin (also known as Adriamycin) is the subject of U.S. Pat. No. 3,590,028 and is a prescribed antineoplastic agent used in a number of chemotherapeutic treatments. Specifically, doxorubicin and daunomycin have the formula:

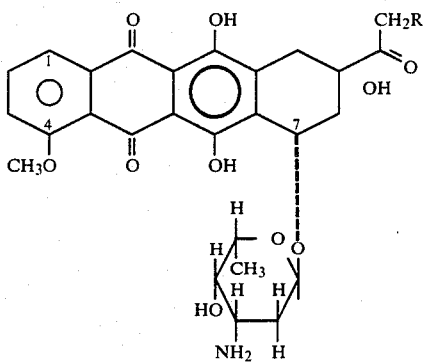

with the compound being doxorubicin when R is —OH and daunomycin when R is —H.

In view of the proven effectiveness of known anthracyclines in the treatment of cancer, efforts have been undertaken to develop less toxic derivatives which can be administered in high, more effective dosages with greater frequency.

U.S. Pat. No. 4,046,878 to Patelli et al. discloses daunomycin analogues substituted at the 1-position and/or the 4-position with chlorine or bromine.

SUMMARY OF THE INVENTION

The present invention relates to compounds represented by the formula (I)

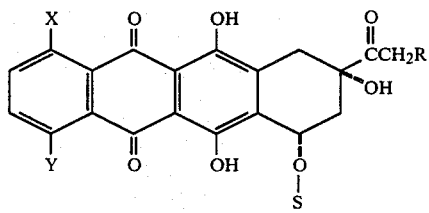

wherein R is hydrogen or hydroxyl, one of X and Y is fluorine and the other is hydrogen, or both X and Y are fluorine, and S is a sugar moiety represented by the formula (II)

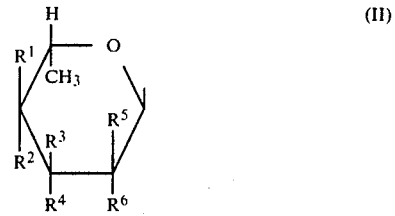

wherein one of $R^1$ and $R^2$ is hydrogen and the other is hydroxy or acyloxy; one of $R^3$ and $R^4$ is hydrogen and the other is hydrogen, hydroxy, acyloxy or amino; and one of $R^5$ and $R^6$ is hydrogen and the other is a halogen atom selected from the group consisting of fluorine, chlorine, bromine and iodine. Suitable acyloxy groups have 2 to 4 carbon atoms, the most typical example being O-acetyl.

Still more particularly, the present invention is directed to compounds of the formula (I) wherein S is a 2,6-dideoxy-2-halo-hexopyranose sugar.

Still more particularly, the present invention is directed to 3'-deamino-2'-halo derivatives of 4-fluoro-, 1-fluoro- or 1,4-difluoro- 4-demethoxydaunomycin or 4-demethoxydoxorubicin.

The present invention also provides pharmaceutical preparations containing the aforesaid compounds in therapeutically effective amounts in suitable carriers.

The compounds of the present invention have been shown to be effective against lymphoblastic leukemia in the P388 leukemia screen. In addition, it is also anticipated that the compounds of the present invention will be effective in the treatment of other tumors such as ascitic tumors, solid tumors such as sarcoma 180, and L1210 leukemia.

Certain of the compounds of the present invention are also available in the form of acid addition salts. Suitable salts include hydrochlorides, citrates, formates, etc.

Therapeutic compositions containing the novel compounds of the present invention as active agents can be prepared by dispersing or dissolving the compound in any pharmaceutically acceptable, non-toxic carrier suitable for the desired mode of administration. Therapeutic compositions of the present invention may be administered parenterally by intravenous, intraperitoneal, or other conventional injection or orally in some cases. Preferably, the carrier is an aqueous medium buffered to pH 7.2 to 7.5, the physiological range. Any suitable conventional buffer can be used such as tris phosphates, bicarbonates or citrates. If desired, saline solution can be used, with pH adjustment and buffering. Optimal dosages may vary over a broad range from approximately 0.1 to 20 mg/kg of body weight depending upon the particular compound and mode of administration employed.

The present invention also provides a method for inhibiting the growth of mammalian tumors comprising administering a therapeutically effective amount of the aforesaid compounds to animals afflicted with such tumors.

DETAILED DESCRIPTION OF THE INVENTION

Examples of antibiotics in accordance with the present invention include 3'-deamino-4-demethoxy-3',4'-di-O-acetyl-4-fluoro-2'-iododaunomycin and 3'-deamino- 4-demethoxy-3',4'-di-O-acetyl-4-fluoro-2'-iododoxorubicin; 3'-deamino-4-demethoxy-4-fluoro-2'-iododaunomycin and 3'-deamino-4-demethoxy-4-fluoro-2'-iododoxorubicin; 3'-deamino-4-demethoxy-1-fluoro-2'-iododaunomycin and 3'-deamino-4-demethoxy-1-fluoro-2'-iododoxorubicin. A particularly preferred class of compounds are the 4'-epi derivatives of the aforementioned compounds.

The compounds of the present invention can be prepared from aglycones obtained by the synthesis outlined in U.S. application Ser. No. 692,584, filed Jan. 18, 1985 (which is hereby incorporated herein by reference). They can be prepared by reacting a cyanophthalide anion of the formula (III)

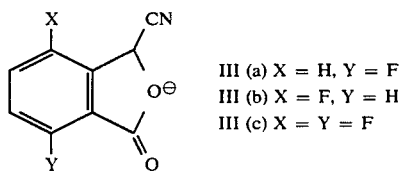

III (a) X = H, Y = F
III (b) X = F, Y = H
III (c) X = Y = F wherein X and Y are defined as above with a quinone monoketal of the formula (IV)

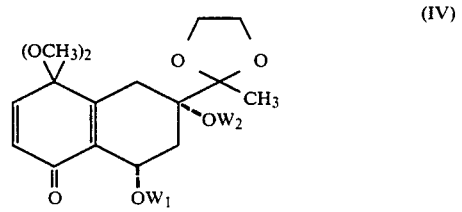

(IV)

where at least one of $W_1$ and $W_2$ is a protecting group and the other is hydrogen. The resulting anthracyclinone can be coupled with an appropriate sugar using the approach of Acton et al., *J. Med. Chem.*, 17, 659 (1973).

The required cyanophthalides IIIa-c were obtained by two general routes. The first involves ortho-metallation of the dimethylacetal (V) followed by reaction with carbon dioxide and hydrolysis to afford the hydroxyphthalide (VIa).

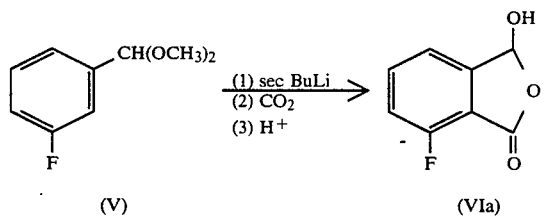

The above chemistry was less convenient for the preparation of hydroxyphthalides (VIb,c) and an alternative route was employed for these latter two compounds. The required oxazolines (VIIb,c), prepared by standard methods [see J. W. Conforth, *Heterocyclic Compounds* 5, 386 (1957); A. I. Meyers and D. L. Temple, *Journal of the American Chemical Society* 92, 6654 (1970) and 92, 6646 (1979)] from the corresponding carboxylic acids, were ortho-metallated and reacted with dimethylformamide. Acid hydrolysis of the product from this reaction followed by standard isolation as detailed in Synthesis Examples 2 and 3 furnished the required hydroxy phthalides (VIb) and (VIc).

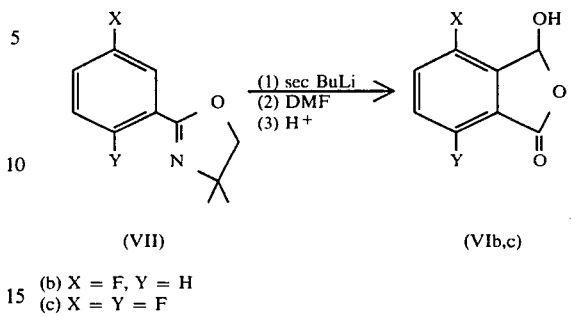

(b) X = F, Y = H
(c) X = Y = F

The cyanophthalides (IIIa-c) were then prepared by reaction with alkali metal cyanide, acidification, and then cyclization with Vielsmeier reagent by a procedure similar to that described in U.S. application Ser. No. 692,584, filed on Jan. 18, 1985. Details are presented in Examples 1-3.

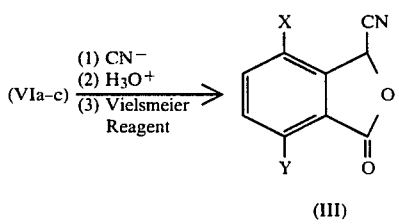

(a) X = H, Y = F
(b) X = F, Y = H
(c) X = Y = F

Quinone monoketals useful in the present invention are available from thallium oxidation of p-methoxyphenols or anodic oxidation of 1,4-dimethoxybenzenes followed by mild acid hydrolysis. They are best obtained by anodic oxidation of 1,4-dimethoxy aromatic systems followed by monohydrolysis of the quinone bisketal.

For a discussion of the synthesis of quinone monoketals, reference may be made to Swenton, Jonn S., "Anthracyline Antibiotics," H. El Khadem, Ed.; Academic Press, Inc." New York, 1982; Dolson et al., supra; Chenard et al., "Annelation Reaction of Quinone Monoketals Studies Directed at an Efficient Synthesis of Anthracyclinones," *J. Org. Chem.* 49, 318-325 (1984); and J. S. Swenton, *Acc. Chem. Res.* 16, 74-81 (1983).

Much of the work which has been done using annelation reactions has been done using quinone monoketals in which the oxygen functions at the eventual C-7 and C-9 positions have a trans relationship. Epimerization of the C-7 oxygen and separation of the isomers are required to obtain the active antibiotic. The separations of anthracyclinones such as (±) 4-demethoxydaunomycinone and (±) daunomycinone from their epi-isomers is particularly difficult. Consequently, in the preferred synthesis the correct A-ring stereochemistry is established early, before the tetracyclic structure is formed.

In accordance with the preferred embodiments of the present invention, the quinone monoketal is synthesized with the C-7 and C-9 oxygens in cis-relationship. This can be accomplished using the reaction sequence taught by Swenton, "Anthracycline Antiobiotics" p. 189 or by the following route:

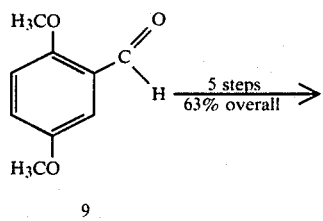
9
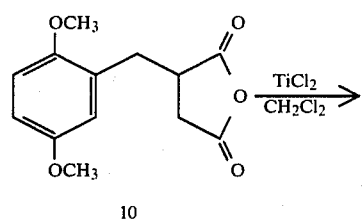
10
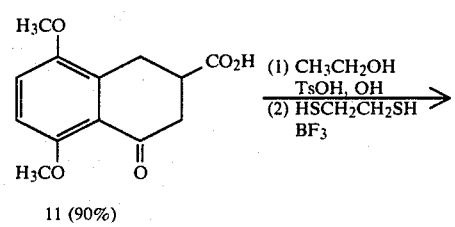
11 (90%)
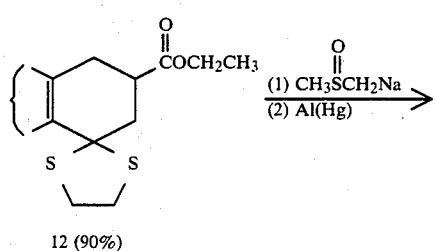
12 (90%)
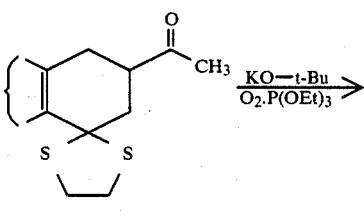
13 (98%)
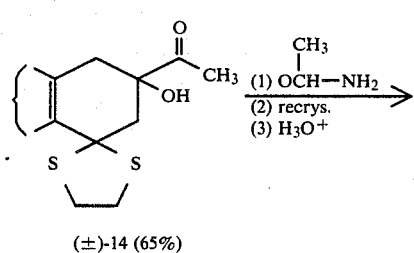
(±)-14 (65%)
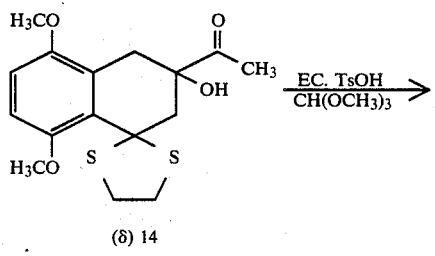
(δ) 14
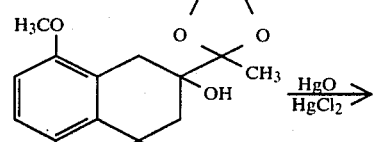
15
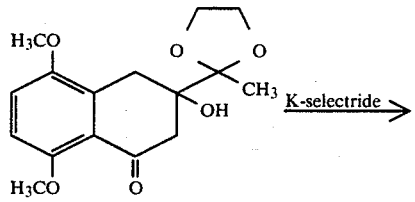
16
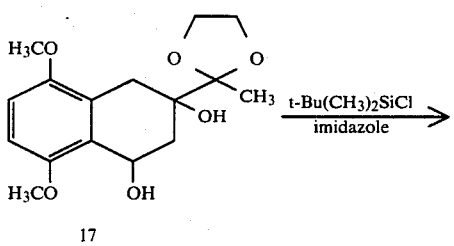
17
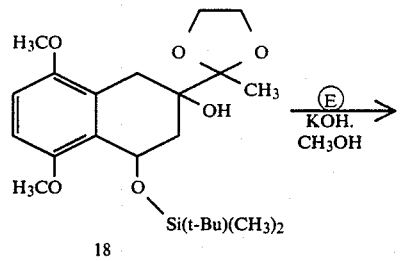
18
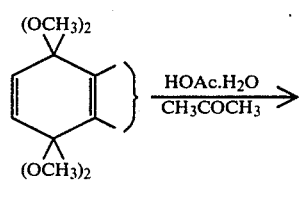
19
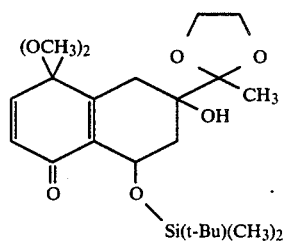
20
The basic bicyclic system 11 is prepared by the general approach of Wong and Schwenk, *Can J. Chem.*, 49, 2712 (1979). These procedures, detailed in the examples below, allow preparation of 10 in 63% overall yield with no purifications except a simple recrystallization in the final step. The liquid hydrogen fluoride cyclization of the anhydride 10 to the tetralone 11, while useful in small-scale work, is impractical for large-scale synthesis. Althougn a number of other Friedel-Crafts catalysts do not give good yields in the 10 to 11 conversion, titanium tetrachloride in methylene chloride effects the ring closure reproducibly on a 100 gram scale in 90% yield.

The two CO groups of 11 are differentiated chemically by esterification followed by thioketalization to give 12. Several attempts were made to introduce the hydroxyl group alpha to the ester function in 12. Oxygenation of the ester enolate of 12 proved difficult. Oxygenation with oxodiperoxymolybdenum (pyridine) (hexamethylphosphoric triamide), the $MoO_5$ HMPA reagent, gives a complex mixture of products. Apparently, oxidation of the thioketal competes with enolate oxidation. Oxygenation of the ester enolate with oxygen in the presence of triethylphosphite gives primarily recovered starting material.

The preferred method involves conversion of the ester to the ketone via the Corey procedure (*J. Am. Chem. Soc.*, 87 1345 (1965). This conversion was initially conducted on the methyl ester of 12; however, the yields of the reaction were quite variable, and poor yields were obtained on larger scale (50 g) reactions. Surmising that part of the difficulty comes from the high insolubility of the methyl ester in the solvent system, the reaction was then performed on the lower-melting and more soluble ethyl ester. Using the ethyl ester 12, the conversion to 13 was conducted routinely on a 100-gram scale in over 90% yield. The required tertiary hydroxyl group is then introduced via oxygenation of the ketone enolate. The yields for this oxygenation were only reproducible when freshly distilled dimethylformamide was employed as solvent and the oxygen uptake monitored. Otherwise, an induction period was often noted, and, unless the reaction was quenched at the proper time, low yields of 14 resulted. The results of this oxygenation are surprising. It might have been anticipated that the reaction would fail since the sulfur of the thioketal could be easily oxidized by the hydroperoxide intermediate formed in the reaction.

The racemate 14 can be resolved using $S(-)-\alpha$-methylbenzylamine. Since both antipodes of the amine are commercially available, a successful resolution affords the molecule of natural absolute configuration. Reaction of 14 with $S(-)-\alpha$-methylbenzylamine followed by recrystallization from ethyl acetate affords a 25% yield of optically pure imine which is hydrolyzed to a levorotatory hydroxy ketone, $(-)$-14. While the yield of the resolution is only 25%, the enriched imine recovered from the initial resolution can be hydrolyzed, and the enriched (R)-14 reacted with $R(+)-\alpha$-methylbenzylamine to afford after resolution and hydrolysis pure (R)-14. The mother liquors from this sequence of reactions are then resolved with $(-)-\alpha$-methylbenzylamine to afford additional (S)-14. In practice, two such cycles gave a 35% yield of (S)-14 from racemic 14. Conversion of $(-)$-14 to natural daunomycinone (vide supra) establishes the configuration of 14 as the desired natural configuration.

Ketalization of 14 under standard azeotropic conditions sometimes leads to decomposition products as well as the desired ketal, out mild ketalization conditions give the ketal 15 in quantitative yield. Various methods for reduction of 16, available from thioketal hydrolysis of 15, afford a difficultly separable cis/trans mixture of diols. However, potassium tri-sec-butylborohydride (K-selectride) reduction of 16 affords almost exclusively the required cis-diol 17.

Previous studies of the annelation reaction with the phenylsulfonyl anion indicated that it was necessary to protect the tertiary OH group to obtain modest yields of tetracyclic product. Since the benzylic OH group of 17 needs to be protected for the anodic oxidation step leading to the quinone bisketal, various methods for protecting both OH groups in 17 were examined. While the benzylic hydroxyl group is easily functionalized, functionalization of both it and the tertiary OH group of 17 could not be performed cleanly with either t-butyldimethylsilyl chloride or chloromethylmethyl ether. Apparently, the steric bulk of the ethylene glycol ketal and the other cis oxygen substitutent hinders functionalization of the tertiary position. The difficulty in protecting both hydroxyl groups led to the examination of the chemistry of the monoblocked system 18.

Anodic oxidation of 18 in a single cell produces in excellent yield the respective quinone bisketal, 19, which is directly hydrolyzed to a mixture of two regioisomeric monoketals in a ratio of ca 83:17 as determined by HPLC analysis. The major isomer, whicn could be obtained in a pure form by recrystallization, was assigned as 20 by analogy to the directing effect of an allylic oxygen substitutent on model quinone bisketal hydrolyses. This assignment was subsequently confirmed by the use of the monoketal in the synthesis of (+)-daunomycinone.

The quinone monoketal is then reacted with the cyanophthalide anion as follows:

$$(III) + 20 \xrightarrow[(2) H_3O^+]{(1) 0° C.}$$

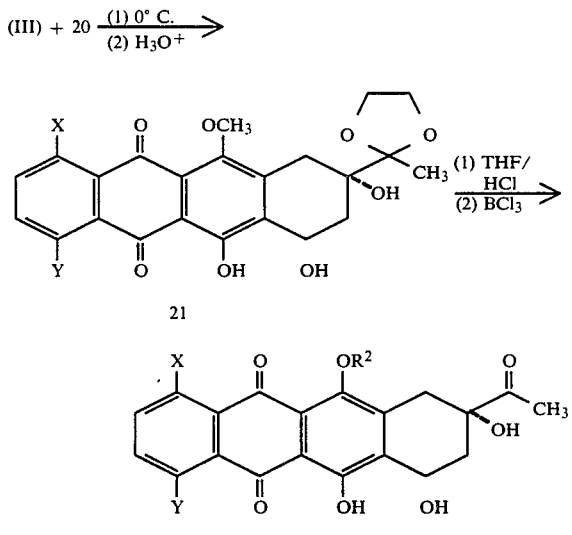

22a. $R^1 = H, R^2 = CH_3$ (98%)
22b. $R^1 = OCH_3, R^2 = CH_3$ (84%)

The annelation reaction is typically conducted at 0° C. The highest yields have been obtained using a homogeneous medium of tetrahydrofuran and DMSO as the solvent and dimsyl anion as base. Those skilled in the art will appreciate that other solvent and base systems can be used with varying results. Potentially useful solvents include ethers (especially 1,2-dimethoxyethane), alcohols (especially t-butyl alcohol), dimethylformamide, and hexamethylphosphoramide. Potentially useful bases include alkali and ammonium hydroxides (especially under phase transfer conditions), metal alkoxides [especially alkali, cesium (III) salts, and t-butyl alkoxides], and alkali metal salts of hindered amines.

A proposed laboratory technique for reacting the cyanophthalide and the quinone monoketal is to add methyl lithium dropwise to a 0° solution of DMSO and THF (V/V=52:130). The cyanophthalide in DMSO is then added over about 1 minute. After stirring for 5 minutes, the solution is cooled to aoout −40°, and the monoketal 20 in THF is added rapidly. The cooling bath is removed and the mixture is stirred for several hours at room temperature.

Hydrolysis of the ketal and demethylation of the aromatic methoxyl group gives the anthracyclinone an excellent overall yield.

Anthracycline aglycones prepared in accordance with the present invention can be coupled with a sugar such as daunosamine according to the teachings of Acton et al, supra, to produce the antibiotic or using other coupling reactions known in the art. The reaction of the anthracyclinone with a 1'-chlorosugar in a Koenigs-Knorr reaction is often used. See also U.S. Pat. No. 4,067,969.

While the synthesis has been illustrated for daunomycinones, it can also be used to prepare the adriamycinones. The anthracyclinones available from this chemistry can be functionalized at the C-14 methyl group as outlined by Arcamore et al. in U.S. Pat. Nos. 4,046,878, 4,039,663 and 4,325,947. Typically, this involves bromination at C-14 followed by treatment with aqueous sodium formate.

The 2'-halo derivatives of the present invention are preferably prepared from 1,6-anhydro-3,4-di-O-acetyl-2,6-dideoxy-hex-1-enitols such as 3,4-di-O-acetyl-L-fucal or 3,4-di-O-acetyl-L-rhamnal. These sugars can be prepared as described in B. Iselin and T. Reichstein, *Helv. Chim. Acta*, 27, 1146, 1200 (1944).

The aglycon is usually reacted with 3,4-di-O-acetyl-L-rhamnal or 3,4,-di-O-acetyl-L-fucal in an anhydrous mixture of acetonitrile and tetrahydrofuran followed by the addition of a halogenating agent such as N-iodosuccinimide or N-bromosuccinimide. The halogenating agent is generally used in a stoichiometric excess, e.g., 1.5 to 3 times the amount of the aglycon on a molar basis. This synthesis is described in U.S. Pat. No. 4,427,664 to Horton et al. 4'-Halo derivatives can be prepared in a manner analogous to that described in European Patent Specification No. 81107618.1 and U.K. Application No. 2,118,540 published Nov. 2, 1983.

The invention is illustrated in more detail by the following non-limiting examples. Unless otherwise indicated, all temperatures are given in degrees Celsius.

SYNTHESIS EXAMPLE 1 a. 3-Hydroxy-7-fluoro-1(3H)-isobenzofuranone. To a −70° C. solution of the dimethylacetal of 3-fluorobenzaldehyde (5.3 g, 31 mmol) in THF (35 ml) was added dropwise sec-butyllithium (22.2 ml of a 1.4 M solution in hexane), and the red solution was stirred for 0.5 h. The solution was saturated with $CO_2$ for 5 min with the red color dissipating to yield a light yellow solution. After 10 min the reaction was allowed to warm to room temperature, and after 30 min HCl (3.5 ml) was added. After concentration the solution was made basic with 5% KOH (25 ml), the neutral material extracted with $Et_2O$ (2×40 ml), the base layer acidified to pH 1 with HCl, and the product extracted witn EtOAc (2×75 ml). Work up as usual afforded 4.5 g (86%) of the title compound, mp 11°–119°, suitable for use in the next step. Recrystallization of this material from EtOAc/PE gave analytically pure material: mp 126°–127° C.; IR 3400 (br s), 1740–1760 (structured s), 1630 (m), 1485 (m), 1300 (m), 1085 (s), 910 (m), 760 (m); $^1H$ NMR 7.8–7.1 (highly structured m, 3 H), 6.60 (or s, 1H); exact mass calcd for $C_8H_5O_3F$ m/e 168.0227, obsd 168.0226.

b. 3-Cyano-7-fluoro-1(3H)-isobenzofuranone. A solution of KCN (2.1 g, 30.8 mmol), water (3.5 ml), and the products of part a (0.71 g, 4.2 mmol) was cooled to 0° C. Concentrated HCl (14 ml) was added, and the solution was stirred for 10 min and then extracted with EtOAc (3×50 ml). Workup as usual gave a yellow-orange oil which was dried under vacuum, dissolved in $CH_3CN$ (8 ml), and added to the Vilsmeier salt prepared from oxalyl chloride (1.3 g) and DMF (1.23 ml) in the usual manner. After stirring for 1 min at 0° C., pyridine (1.7 ml) was added, and the solution was stirred for an additional 15 min. Workup as for the parent system gave a dark red oil which was recrystallized from $CH_3OH$ to afford 0.425 g (57% of the title compound in two crops, mp 117°–120° C. An additional crystallization ($CH_3OH$) gave the pure material: mp 121°–123° C.; IR 1780 (s), 1630 (m), 1610 (m), 1490 (m), 1280 (m), 1260 (m), 1070 (m), 1025 (m), 995 (s), 800 (m); $^1H$ NMR 8.0–7.6 (str m, 1 H), 7.6–7.2 (str m, 2 H), 6.1 (s, 1 H); exact mass calcd for $C_9H_4NO_2F$ m/e 177.0227, obsd 177.0233.

SYNTHESIS EXAMPLE 2 a. 4-Fluoro-3-hydroxy-1(3H)-isobenzofuranone. To a −78° C. solution of the oxazoline derivative (7.8 g, 40.4 mmol), prepared from 3-fluorobenzoic acid in the usual manner, in THF (50 mL) was added over 15 min sec-BuLi (29 mL of 1.4 M solution). After 30 min, DMF (6.3 mL) was added, and the reaction mixture was stirred at −78° C. for 2 hr. The reaction was then quenched with water (10 mL), and the mixture was acidified with HCl and allowed to stir for 12 hr. The layers were separated, the aqueous layer was extracted with EtOAc, and the combined organic layer was concentrated in vacuo. This material was dissolved in 5% KOH (50 mL), and the base layer was washed with $Et_2O$ (2×100 mL) to remove neutrals. The resulting base layer was added to 0° C. solution of concentrated HCl (25 mL), and the resulting cold acidic solution was extracted with EtOAc (3×75 mL). Workup and drying gave a tacky yellow solid (4.4 g) which was recrystallized from $CHCl_3$ to give the title compound (1.97 g, 30%), mp 97°–100° C.

b. 4-Fluoro-3-cyano-1(3H)-isobenzofuranone. The above hydroxyphthalide (0.5 g, 3.0 mmol) and KCN (1.5 g) were dissolved in water (5 mL) and cooled to 0° C. A little ice was added followed by dropwise addition of concentrated HCl (10 mL), whereupon the solution turned cloudy. The mixture was stirred for 5 min and then extracted with EtOAc (2×75 mL). Workup and drying gave a thick yellow oil which was used directly in the next step. To the Vielsmeier salt prepared in the usual way from $CH_3CN$ (7 mL), oxalyl chloride (0.92 g), and DMF (0.86 mL) was added the above material in $CH_3CN$ (6 mL). After stirring for 1 min, pyridine (1.2 mL) was added, and the mixture was stirred an additional 15 min. The reaction mixture was then poured into 5% HCl (75 mL). Extractive workup (EtOAc) and concentration gave an orange/yellow solid which was chromatographed on silica gel ($CH_2Cl_2$ as eluant) to give the title compound (0.36 g, 60%) from hydroxyphthalide as light yellow crystals, mp 93°–96° C.

SYNTHESIS EXAMPLE 3 a. 4,7-Difluoro-3-hydroxy-1(3H)-isobenzofuranone. To a −78° C. solution of the oxazoline derivative (7.95 g, 37.7 mmol), prepared from 2,5-difluorobenzoic acid in the usual manner, in THF (50 mL) was added over 15 min sec-BuLi (29 mL of 1.3 M solution). After 30 min, DMF (6.0 mL) was added, and the reaction was stirred at −78° C. for 2 hr. The reaction was then quenched with concentrated HCl (5 mL). The solvents were removed in vacuo, and the residue was taken up in 5 N HCl (5 mL) and heated on the steam bath overnight. After cooling to room temperature, the reaction mixture was extracted with EtOAc (3×200 mL). Standard workup gave a light brown solid (6.5 g, 93%, mp 125°–128° C.).

b. 4,7-Difluoro-3-cyano-1(3H)-isobenzofuranone. The above hydroxy phthalide (3 g, 16.1 mmol) and NaCN (7.5 g) were dissolved in water (15 mL) and cooled to 0° C. Ice (2 g) was added, followed by dropwise addition of concentrated HCl (60 mL). The mixture was stirred for 5 min and then extracted with EtOAc (3×50 mL). Workup and drying gave a thick yellow oil which was used directly in the next step. To the Vielsmeier salt prepared in the usual way from $CH_3CN$ (39 mL), oxalyl chloride (3.4 mL), and DMF (4.6 mL), was added the above material in $CH_3CN$ (30 mL). After stirring for 1 min, pyridine (7.2 mL) was added, and the mixture was stirred an additional 15 min. The reaction mixture was then poured into 5% HCl (200 mL). Extractive workup (EtOAc, 3×75 mL) and concentration gave an orange/yellow solid which was chromatographed on silica gel ($CH_2Cl_2$ as eluant) to give the title compound (1.5 g, 48%) from hydroxy phthalide as light yellow crystals, mp 87°–89° C.

SYNTHESIS EXAMPLE 4

Dimethyl-(2,5-dimethoxybenzylidine) malonate. A mixture of 2,5-dimethoxybenazldehyde (300 g, 1.8 mol), dimethymalonate (240 ml, 262 g, 1.98 mol), piperidine (9.0 ml), HOAc (3 ml), and benzene (300 ml) was heated to reflux in an apparatus equipped with a Dean-Stark trap (34 ml of lower phase was collected over 14 hr). The mixture was diluted with an equal volume of $Et_2O$ and washed with 100 ml portions of 5% HCl, 5% $NaHCO_3$, and brine. Concentration in vacuo yielded a yellow oil which was diluted with $Et_2O$/H and cooled to give dimethyl-(2,5-dimethoxybenzylidene) malonate (471 g, 93%) as yellow crystals suitable for use in the next step. A sample recrystallized from $Et_2O$ showed: mp 59°–60°; IR 2950 (m), 1740 (s,) 1725 (s), 1620 (m), 1500–1400 (m, structured), 1272–1150 (s, structured); $^1$H-NMR (60 MHz, $CCl_4$) 7.80 (s, 1H), 6.78 (m, 3H), 3.75 (overalapping s, 6H), 3.68 (s, 3H), 3.60 (s, 3H); exact mass calcd for $C_{14}H_{16}O_6$ m/e 280.0947, obsd 280.0936.

SYNTHESIS EXAMPLE 5

Trimethyl-3-(2,5-dimethoxyphenyl)-1,2,2,-propanetricarboxylate. A mixture of the product from Synthesis Example 4 (100 g, 0.36 mol) and 10% Pt-C (2.0 g) in THF (225 ml) was hydrogenated in a Paar apparatus (initial pressure 59 lb/in.$^2$, final pressure 27 lb/in.$^2$) for 5 hr. The solution was filtered through Celite, and the colorless filtrate was used directly in the next step. Distillation of a portion of the material through a short-path head afforded 90% of a colorless viscous oil: bp 172°–174°/0.6 mm; IR (neat) 2970 (s), 1740 (s), 1500 (s), 1440 (s), 1280 (s), 1230 (s), 1160 (s), 1010 (s), $^1$H-NMR (60 MHz, $CCl_4$) 6.60 (m, 3H), 3.80 (s, 3H), 3.70 (s, 3H), 3.65 (s, 6H), 3.58 (obscured, 1H), 3.10 (d, J=7.5 Hz, 2H).

The hydrogenation solution was diluted with sufficient THF to make the total volume about 1 liter and then placed in a 2-1, 3-necked flask under $N_2$ while NaH (17 g, 60% by weight) in mineral oil was added over 1 hr. After $H_2$ evolution ceased, methyl bromoacetate (59.8 g) was added over 15 min. The solution was heated to reflux for 5 hr and then the THF was removed in vacuo to afford a white oily solid (a mixture of product NaBr, mineral oil, and unknown impurities). This material was used directly in the next step. Standard workup of a portion of the material followed by recrystallization of the product from $Et_2O$/PE gave the triester as a white crystalline solid: mp 102.5°–104.0°; IR 1730 (s), 1495 (s), 1426 (s), 1310 (s), 1280 (s), 1220 (s), 1190 (s), 1040 (s); $^1$H-NMR (60 MHz, $CCl_4$), 6.60 (brd, 2H), 6.42 (brd, 1 H), 3.55-3.70 (overlappings, 15H), 3.32 (s, 2H), 2.70 (s, 2H); exact mass calc for $C_{17}H_{22}O_8$ m/e 354.1315, obsd 354.1305.

SYNTHESIS EXAMPLE 6

(2,5-Dimethoxybenzyl) succinic anhydride 10. The crude triester from two runs as described in Synthesis Example 5 [200 g of starting dimethyl-(2,5-dimethoxybenzylidine) malonate] was dissolved in hot EtOH (600 ml), water (1200 ml) and KOH (360 g) were added, and the homogeneous solution was heated to a gentle reflux for 14 hr. The resulting orange solution was cooled and then extracted with $CHCl_3$ (2×400 ml). The light orange aqueous phase was cooled in ice and slowly acidified with conc HCl (600 ml). After 5 hr at 0°, the solid was collected and dried to constant weight under vacuum to afford 182.2 g (81% overall from Knoevenagel product) of white powdery solid.

The crude triacid (182.2 g, 0.584 mol) was added to $Ac_2O$ (1.0 l), and the solution was slowly heated to reflux. The solid gradually dissolved, and $CO_2$ evolution was apparent. After heating for 2 hr, the solution was concentrated by distillation at atmospheric pressure (500 ml of distillate was collected). The resulting cloudy solution was filtered (3.4 g of white solid, probably NaBr, was collected), and the remaining $Ac_2O$ was removed in vacuo at about 80°. The dark brown oil was then poured into a 1 L flask, and the flask was rinsed, using a minimum amount of $CHCl_3$. The solution was rapidly swirled while hexane (about 350 ml) was added, and then the product was allowed to crystallize. After collection of the solid and drying, white anhydride (122 g, 84% from the crude acid) was obtained: mp 74°–76° (lit. mp 75°–76°); IR 1860 (s), 1780 (s), 1500 (s), 1220 (s), 1170 (s), 1140 (s), 928 (s), 915 (s); $^1$H-NMR 6.69 (2s, 3H), 3.75 (s, 3H), 3.73 (s, 3H), 3.20–2.74 (m, 5H).

SYNTHESIS EXAMPLE 7

1,2,3,4-Tetrahydro-5,8-dimethoxy-4-oxo-2-naphthoic acid 11. The anhydride (106 g, 0.42 mol) in $CH_2Cl_2$ (500 ml) was added to a stirred solution of $TiCl_4$ (110.2 ml, 190.6 g, 1.0 mole) in $CH_2Cl_2$ (1600 ml) at room temperature over a period of 20 min. A slight warming of the mixture was noted, and the solution was then stirred at room temperature for 1 hr. The mixture was then cooled in ice, and the $CH_2Cl_2$ layer was poured onto ice (300 g). Some product precipitated and was collected; however, the majority of material remained as a reddish oily solid on the walls of the reaction flask. Water (850 ml) was added to the flask, and the solution was vigorously stirred until the reddish-brown material was converted into a light yellow solid. This material was filtered and combined with the previous solid, washed with water and dried (first in the air and then under vacuum) to obtain the keto acid (95.4 g. 90%), mp 199°–201° (lit. mp 207°–208°), suitable for use directly in the next step; IR 1740 (s), 1680 (s), 1475 (s), 1280 (s), 1270 (s), 1260 (s), 1170 (s), 1080 (s), $^1$H-NMR 6.90 (ABq, $\Delta\nu = 15.6$ Hz, J=9 Hz, 2H), 3.85 (s, 3H), 3.82 (s, 3H), 3.6–2.7 (m, 5H).

SYNTHESIS EXAMPLE 8

Ethyl-1,2,3,4-tetrahydro-5,8-dimethoxy-4-oxo-2-naphthoate

Cyclic 4-(Ethylene mercaptole), 12. A mixture of the keto acid from Synthesis Example 7 (142 g 0.57 mol), abs EtOH (100 ml), benzene (550 ml), and p-TsOH (0.5 g) was heated to reflux under a 39 cm Vigreux column and a Dean-Stark trap. The pot temperature was adjusted so that the benzene/EtOH/H$_2$O azeotrope distilled, and the reaction was allowed to proceed for 24 hr. Conventional workup afforded 95% of the ester as a light tan solid. Recrystallization of this material from EtOH afforded the ethyl ester as a white solid: mp 96°–98°; IR 1730 (s), 1680 (s), 1585 (s), 1475 (s), 1255 (br s), 1085 (s); $^1$H-NMR (60 MHz) 6.88 (AB q, $\Delta\nu = 15$ Hz, J=9 Hz, 2H), 2.23 (l, J=6 Hz, 2H), 3.85 (s, 3H), 3.82 (s, 3H), 3.39–2.82 (m, 5H) 1.23 (t, J=6.5 Hz, 3H); exact mass calc for C$_{15}$H$_{18}$O$_5$ m/e 278.1154, obsd 278.1162.

More conveniently, the solvent from the crude esterification mixture was distilled at atmospheric pressure, and the solid residue was dried under vacuum for several hours. To this mixture were added benzene (1.5l), 1,2-ethanedithiol (0.432 mol) and BF$_3$ Et$_2$O (0.5 ml). This mixture was heated to reflux under a Dean-Stark trap for 12 hr, and then the solvent was distilled at atmospheric pressure until the volume of the reaction mixture was about 150 ml. The cooled mixture was then diluted with an equal volume of PE and cooled in ice. The title compound, obtained as a tan solid (184 g, 90%, mp 107°–109°), was used directly in the next step. A sample recrystallized from benzene/H gave wnite crystalline material; mp 114°–116°; IR 2950 (m), 2930 (m), 1725 (s), 1590 (m), 1475 (s), 1460 (s), 1285 (s), 1255 (s), 1065 (s); $^1$H-NMR (90 MHz) 6.75 (s, 2H), 4.21 (q, J=7.6 Hz, 2H) 2.86 (s, 3H), 3.76 (s, 3H), 3.57–3.42 (m, 4H), 3.2–2.3 (m, 5H), 1.31 (t, J=7.5 Hz, 3H); exact mass calc for C$_{17}$H$_{22}$O$_4$S$_2$ m/e 354.0960, obsd 354.0970.

SYNTHESIS EXAMPLE 9

1,2,3,4-Tetrahydro-5,8-dimethoxy-4-oxo-2-acetyl-naphthalene, 13. To a 3-l, round bottomed flask equipped with a stirrer and condenser and maintained under N$_2$ was added NaH (37.8 g of a 60% oil dispersion, 0.95 mol). The NaH was washed with PE (2×25 ml), and DMSO (400 ml) was added. The material was slowly heated to 65°–70° and maintained at this temperature until H$_2$ evolution ceased (2 hr). The mixture was cooled to 0°, and THF (400 ml) was added. The crude product from the previous step (134 g, 0.38 mol) was dissolved in THF (535 ml) and added to the rapidly stirred solution. The ice bath was removed, and the brownish-red solution was stirred for 1 hr and then poured into water (4 l). This mixture was carefully acidified to pH 4 by dropwise addition of conc HCl, and the solution was extracted with CH$_2$Cl$_2$ (4×750 ml). The extracts were combined and washed with water (2×2500 ml), the bulk of the solvent was removed by distillation at atmospheric pressure, and the remaining volatiles were removed from the thick yellow oil by vacuum drying for 14 hr. The crude ketosulfoxide showed: $^1$H-NMR 6.78 (s, 2H), 4.00 (s, 2H), 3.89 (s, 3H), 3.82 (s, 3H), 3.51–3.39 (m, 4H), 3.20–3.00 ), (m,5H), 2.71 (s, 3H).

The material was dissolved in THF and divided into two batches for the Al/Hg reduction. Aluminum foil (57 g, 1-in. squares) was placed in a 5-l, 3-necked, round-bottomed flask equipped with an efficient condenser and an overhead stirrer, and 2% aqueous HgCl$_2$ (1.0l) was added. The solution was swirled for 30 sec, then the HgCl$_2$ solution was poured off, and a solution of the compound in THF (2400 ml) was added, followed by addition of water (250 ml).

The Al is very reactive after amalgamation. Consequently, these steps must be done rapidly since a fire could result. The reaction must be monitored closely since it becomes sufficiently exothermic that cooling must be employed; however, the reaction temp should be maintained above 50°. After 2 hr, the H$_2$ evolution ceased, and the mixture was filtered through Celite. The THF was removed in vacuo and then used to wash the aluminum salts; this process was repeated three times. The product solidified upon concentration to afford 98 g (80%) of light yellow solid, mp 124°–129°, which was used directly in the next step. The yield of product varied from 80% to as high as 95% on 50 gram runs. A sample recrystallized from EtOAC/H showed: mp 128°–130°; IR 1710 (br s), 1600 (m), 1475 (br s) 1435 (s), 1280 (s), 1255 (s), 1090 (s); $^1$H-NMR (90 MHz) 6.75 (s, 2H), 3.38 (s, 3H), 3.74 (s, 3H), 3.6–3.39 (m, 4), 3.1–2.45 (m, 5H). 2.26 (s, 3H); exact mass calc for C$_{16}$H$_{20}$O$_3$S$_2$ m/e 324.0854, obsd 324.0861.

SYNTHESIS EXAMPLE 10

1,2,3,4-Tetrahydro-5,8-dimethoxy-4-oxo-2-acetyl-2-hydroxy naphthalene, 14. To a stirred −24° C. solution of the ketone (8.9 g, 27.4 mmol), t-BuOH (23 ml), freshly distilled DMF (71 ml), and (EtO)$_3$ P (5 ml, 27.4 mmol) maintained under N$_2$ was added a −50° solution of t-BuOH (6.2 g, 55.2 mmol) in DMF 26 ml O$_2$ was introduced into the system and after 15 min one equivalent of O$_2$ (670 ml) was absorbed. The light orange mixture was then quenched by addition of HOAc (5 ml) affording a light yellow mixture. Two such runs were combined and concentrated at 60°/0.2 mm and the residue worked up as usual to afford a light yellow syrup. The majority of remaining volatiles were removed at room temp/10$^{-3}$ mm over 24 hr. Trituration of the resulting semi-solid with Et$_2$O/EtOAc afforded in two crops 12.2 g(65%) of light yellow solid, mp 143°–147° suitable for use in the next step. Recrystallization of this material from EtOAc gave in three crops 10.6 g (56%) of crystalline hydroxy ketone, mp 148°–150°. The analytically pure material showed mp 151°–153° (lit. mp 152.5°–153.0°).

Resolution of (±)-14. A mixture of (±)-14 (4.8 g, 0.014 mol), benzene (100 ml), Linde 4 Å sieves (10 g), and (+)-α-methylbenzylamine (3.6 ml, 0.028 mol) was heated to reflux overnight in an apparatus equipped with a Dean-Stark trap. The mixture was then filtered through a Celite pad and concentrated in vacuo to afford, after trituration with Et$_2$O, the diastereomeric imines as an off-white powder, mp 165°–178°. The ratio of the diastereomeric imines can be determined by integration of the Me groups at about 1.35 in the 200 MHz $^1$H-NMR spectrum. In a typical run this crude product was dissolved in boiling EtOAc (40 ml), and then the volume was reduced to 25 ml. Slow cooling to room temperature gave clear crystals which were filtered, washed with EtOAc (10 ml) and Et$_2$O (15 ml), and dried to yield 1.55 g (25%) of colorless needles: mp 195–195.5; $[\alpha]_D^{20}$ (dioxane)=−29.5°; IR (K Br) 3240 (m), 1660 (s), 1475 (s), 1460 (s), 1435 (s), 1260 (s), 1250 (s), 1080 (s); $^1$H-NMR (200 MHz, C$_6$D$_6$) 7.25–7.00 (m, 5H), 6.51 (AB a, J=4.4 Hz, Δv=12.9 Hz, 2H) 4.37 (q, J=6 Hz, 1H), 3.55 (s, 3H), 3.4–3.3 (m, 2H), 3.29 (s, 3H), 3.17–2.75 (m, 7H), 1.42 (s, 3H), 1.25 (d, J=6 Hz, 3H); exact mass calc for C$_{24}$H$_{29}$NO$_3$S$_2$ m/e 443.1588, obsd 443.1600.

The combined mother liquors were concentrated in vacuo and then hydrolyzed to enriched (s)-14 by adding THF (30 ml) and 5% aqueous HCl (7 ml). This solution was stirred at room temp for 0.5 hr, and then the THF was removed in vacuo. The aqueous layer was extracted with CH$_2$Cl$_2$ (3×30 ml), and the combined organic phases were worked up as usual to afford an oil which crystallized on standing. This hydroxy ketone enriched in (S)-14 was reacted as described above except with (−)-α-methylbenzylamine to yield 1.81 g (29%) of imine: mp 195–195.5%; $[\alpha]_D^{20}$ (dioxane)=+29.5°. Note that this latter imine is the compound having the natural configuration of the anthracyclinone A-ring.

A solution of 5% aqueous HCl (25 ml) was added to a stirred solution of the imine above (3.05 g, 8.9 mmol) in THF (110 ml). The resulting light yellow solution was stirred for 10 min at room temperature and then concentrated in vacuo to remove the majority of the THF. The residue was extracted with CH$_2$Cl$_2$ (3×30 ml) and worked up as usual to afford the levorotatory hydroxy ketone, (s)-14. Recrystallization of this material from EtOAc gave 2.05 g (89%) of white product: mp 178.5°–179.5°; $[\alpha]_D^{20}$ (CHCl$_3$)=24.4° [lit. mp 178.5°–179.5°, $[\alpha]_D^{20}$ (CHCl$_3$)=−24.4°].

SYNTHESIS EXAMPLE 11

1,2,3,4-Tetrahydro-5,8-dimethoxy-4-oxo-2-acetyl-2-hydroxynapthalene. Cyclic 4-(ethylene mercaptole), cyclic 2-ethylene-glycol ketal, 15. A mixture of ketone 14 (61.7 g, 0.18 mol), distilled ethylene glycol (312 ml), commercial trimethylorthoformate (240 ml), and anhydrous p-TsOH (1 g) was combined in the above order and stirred in an oil bath at 37°–40° for 24 hr. The heterogeneous solution (white solid in a blue liquid) was poured into 20% KOH (1200 ml) and stirred for 1.5 hr in an ice batn. The solution was then diluted with water (2 l), stirred for an additional hour, and then filtered. Drying the white solid overnignt in vacuo gave the ketal as a cream-colored solid (69 g, 100%), mp 163°–166° (mp 162.4°–163°).

For (S)-15 the homogeneous mixture was poured into 20% CH$_3$OH/KOH, and after 30 min, ice was added to precipitate the crude solid. The optically pure material showed: mp 130°–131° $[\alpha]_D^{20}$ (CHCl$_3$−38.0°, [lit. mp 144°–146°, $[\alpha]_D^{20}$ (CHCl$_3$)=−42.4°].

SYNTHESIS EXAMPLE 12

Compound 17. The thioketal 15 (22.0 g, 57.3 mmol) was dissolved in CH$_3$OH (3200 ml) and water (400 ml), and to the vigorously stirred mixture were added HgCl$_2$ (22 g, 81 mmol) and yellow HgO (16.6 g, 77 mmol). The progress of the reaction was monitored by TLC (Et$_2$O, phosphomolybdic acid spray, starting material is blue with R$_f$0.4 and product is much less intense with R$_f$0.1), and the reaction was judged complete after 20 min. The solution was filtered through Celite and concentrated at about 50°–55° in vacuo until the volume was about 500 ml. The filtered Hg-salts were slurried with CH$_2$CL$_2$ (3×300 ml) and this solvent was used for extraction of the product from the concentrated aqueous solution. Workup gave 15.4 g (88%) of the β-hydroxy ketone as a light yellow solid which was used directly in the next step, mp 173°–176° (lit. mp 177.5–178.0).

The optically pure material showed: mp 182°–183°, $[\alpha]_D^{20}$ (CHCl$_3$)=+13.9° [lit. mp 182.5°–184.0°, $[\alpha]_D^{20}$ (CHCl$_3$=+14.0°].

A slurry of the crude hydroxy ketone (15.4 g, 0.05 mol) from above in THF (500 ml) was cooled in dry ice for about 0.5 hr. and then potassium tri-sec-butyl-borohydride (100 ml of a 1M THF solution, 0.1 mol) was added dropwise over 0.5 hr. The solution was stirred for 1 hr at dry ice temperature and then for 2 hr at room temperature. The homogeneous yellow solution was cooled in ice, and 20% KOH (225 ml) was added cautiously followed by dropwise addition of 30% H$_2$O$_2$ (48.6 ml). The solution was stirred at room temperature for 1 hr, and then the excess peroxide was destroyed by addition of sodium thiosulfate. After concentration in vacuo, the aqueous solution was extracted with CH$_2$Cl$_2$ (3×200 ml). Workup and trituration with Et$_2$O gave a light yellow crystalline solid. This material was crystallized from CH$_2$Cl$_2$/Et$_2$O to give 13.7 g (89%) of diol, mp 125°–126.5°.

The optically pure material showed: mp 141°–143°, $[\alpha]_D^{20}$ (CHCl$_3$)=+5.3; IR 3530 (br s), 3430 (br s), 1495 (s), 1280 (s.sh), 1275 (s), 1110 (s), 1095 (s), 1080 (s); $^1$H-NMR (200 MHz, D$_2$O wash) 6.66 (s, 2H), 5.14 (br, 1H), 4.03 (s, 4H), 3.81 (s, 3H). 3.75 (s, 3H), 3.08 (dd, J=17.7, 2.4 Hz, 1H), 2.65 (d, J=17.7 Hz 1H), 2.36 (d oft, J=2.4, 2.4, 18.9 Hz, 1H), 1.92 (dd, J=4.9, 18.9 Hz, 1H), 1.42 (s. 3H); exact mass for C$_{16}$H$_{22}$O$_6$ calc m/e 310.1416, obsd 310.1423.

SYNTHESIS EXAMPLE 13

Compound 18. A mixture of the diol 17 (20 g, 0.065 mol), imidazole (20 g, 0.29 mol), t-butyldimethylsilyl chloride (20 g, 0.13 mol) dissolved in dry DMF (200 ml) was stirred at 45° for 24 hr, after which time TLC (ca 80% Et$_2$O/H) showed no starting diol. The bulk of the DMF was removed at 45°/1 mm, and the residue was partitioned between CH$_2$Cl$_2$ (45 ml) and sat. NaHCO$_3$ (200 ml). Standard workup gave a thick oil which solidified to give the protected diol (27 g, 96%) which was used directly in the next step. The analytical sample of the material was obtained by recrystallization from CH$_3$OH/H$_2$O and showed: mp 106°–107°; IR 3440 (m), 1600 (m), 1480 (s), 1465 (m), 1260 (s), 1074 (s), 1045 (m), 980 (m), 850 (m), 780 (m), $^1$H-NMR (200 MHz) 6.7 (center of AB, J=8.7 Hz Δv=21.4 Hz 2H), 5.33 (unresolved t, 1H), 5.29 (s, 1H), 4.03 (s, 4H), 3.76 (s, 6H), 3.12 (dd, J=2.16 Hz, 1H), 2.70 (d, J=16 Hz, 1H), 2.30 (d of poorly resolved t, J= 14 Hz, 1H), 1.81 (dd, J=3.5, 14 Hz, 1H), 1.46 (s, 3H), 0.86 (s, 9H), 0.25 (s, 3H), 0.08 (s, 3H); exact mass for C$_{22}$H$_{36}$O$_6$Si calc m/e 424.2281, obsd 424.2259.

The optically pure compound showed: mp 126°–127°, $[\alpha]_D^{20}$ (CHCl$_3$)=+7.9°.

SYNTHESIS EXAMPLE 14

Compound 19. A slurry of protected diol, 18, (14 g) and 1% KOH/CH$_3$OH (600 ml) was anodically oxidized using the macro Pt electrode and the Pt sheet anode in a thermostated cell held at about 0° with a current of 1 amp. The reaction was followed by UV analysis at 290 nm, and the electrolysis was terminated after the initial optical density decreased to 1% of its initial value (about 3 hr). The mixture was then neutralized with solid CO$_2$ and concentrated on the rotary evaporator. Concentration and drying of the product gave a quantitative yield of bisketal which was hydrolyzed directly to the monoketal. Recrystallization of a sample of the bisketal from Et$_2$OH gave a white crystalline compound: mp 79°–81°.

The optically pure compound showed: m 103°–104° [α]$_D^{20}$ (CHCl$_3$)=18.7°; IR 3470 (s), 29560 (s), 2940 (s), 1110–1080 (vs, br), 1032 (s), 1042 (s), 985 (s); $^1$H-NMR (CCl$_4$ CH$_2$Cl$_2$) 6.06 (s, 2H), 4.73 (distorted t, 1H), 4.58 (s, 1H). 3.87 (s, 4H), 3.12 (s, 3H), 3.09 (s, 3H), 3.06 (s, 6H), 1.8–2.3 (m, 3H), 1.43 (dd, J=3.14 Hz, 1h), 1.23 (s, 3H), 0.87 (s, 9H), 0.15 (s, 3H), 0.10 (s, 3H); $^{13}$C-NMR 139.8 133.8 132.5 131.5 111.8, 95.7, 95.2, 74.8, 65.3, 65.2, 63.9, 61.9, 51.2, 50.8, 50.4 (3 C), 34.8, 31.7, 25.9, 18.5, 17.9, −4.8, −4.7.

A −20° C. solution of 8% HOAc/acetone (75 ml: 300 ml) was added to the crude bisketal, and the homogeneous solution was stored at −20° C. for 48 hr. The solution was then poured into sat. NaHCO$_3$ (150 ml), and the majority of the acetone was removed on the rotary evaporator. The heterogeneous suspension was extracted with CH$_2$Cl$_2$ (2×250 ml), and the organic phase was washed with sat. NaHCO$_3$ (150 ml). The solution was dried and concentrated to give an amber oil which crystallized after being dried under vacuum. The sample was dissolved in boiling Et$_2$O (50 ml), and the Et$_2$O was replaced with low-boiling PE (50 ml). The material was allowed to crystallize at room temperature to afford 9.5 g (64%) of monoketal (20). TLC and 300 MHz $^1$H-NMR analysis showed that this was a 91:9 mixture of regioisomers, mp 108°–110°, suitable for use in the coupling step. A pure sample of monoketal was obtained by careful recrystallization from EtOAc/H:mp 117°–119°; IR 3480 (m), 1660 (s), 1090 (s), 1060 (s), 1045 (s), 1045 (s); $^1$H-NMR (80 MHz) 6.57 (ABq,J=10 Hz,=27.5 Hz, 2H), 5.07 (distorted t, J 2.6 Hz, overlappings 2H), 4.00 (s, 4H), 3.23 (s, 6H), 2.55 (ABq,Δv=31 Hz, J=19 Hz with lower field doublet having J=1 Hz, 2H), 2.17 (d of distorted t, J=19 Hz, 1H), 1.67 (dd, J=3, 19 Hz, 1H), 1.41 (s, 3H), 0.84 (s, 9H), 0.26 (s, 3H), 0.13 (s, 3H); $^{13}$C-NMR [(CD$_3$)$_2$CO] 183.7, 153.0, 144.5, 135.8, 132.3, 112.4, 95.5, 76.6 (2 C), 66.0, 64.0, 50.8, 34.6, 33.4, 26.1 (3 C), 18.9, 18.5, −4.6, −4.9 (1 C missing). (Found: C, 59.82; H, 8.21, Calc for C$_{22}$H$_{36}$O$_7$:C, 60.00; H, 8.18%)

SYNTHESIS EXAMPLE 15

(±)4-Fluoro-4-demethoxydaunomycinone. To a 0° C. solution of DMSO (35 mL) and THF (34 mL0 was added CH$_3$Li (8.9 mL of a 1.29 M solution). After 5 min, 7-fluoro-3-cyano-1(3H)-isobenzofuranone (2.04 g, 11.5 mmol) in DMSO (34 mL) was added, giving a golden brown solution. After an additional 5 min, the monoketal (3.9 g, 8.86 mmol) in THF (34 mL) was added, whereupon the solution turned deep red. The reaction mixture was allowed to stir at room temperature for 2 hr, and then the reaction was quenched by the addition of 5% HCl (100 mL). The majority of the THF was removed in vacuo, (CH$_3$)$_2$CO (250 mL) was added, and the solution was allowed to stir for 12 hr. TLC analysis indicated that the t-butyldimethylsilyl group was not completely removed, CHCl$_3$ was added to render the solution homogeneous, and the reaction mixture was stirred an additional 48 hr. Removal of the majority of the solvent in vacuo afforded a yellow solid which was filtered and dried to give the tetracyclic ketal (3.62 g, 92%, mp 215°–218° C.) which was used directly in the next step. Recrystallization of a portion of this material from CH$_3$OH/CHCl$_3$ gave the analytically pure material: mp 227°–229° C.

A mixture of THF (500 mL) and 30% HCl (180 mL) was cooled to 0° C., and 3.62 g of the above ketal was added. This mixture was then stirred for 24 hr at room temperature, after which TLC analysis showed no change. Additional THF (1200 mL) and concentrated HCl (15 mL) were added, and the solution was warmed to 40° C., whereupon it became homogeneous. After stirring for 48 hr at room temperature, TLC analysis indicated complete hydrolysis of the ketal. The reaction mixture was then concentrated in portions at room temperature, and the resulting slurry was extracted with CHCl$_3$ (3×100 mL), washed with brine, and dried. Concentration and drying in vacuo gave 4-fluoro-4-demethoxy-11-methoxy-11-deoxydaunomycinone (3.0 g, 91%). This material was used directly in the next step.

To a −78° C. solution of the above material (3.0 g) in CH$_2$Cl$_2$ (630 mL) was added BCl$_3$ (80 mL of a 1 M solution in CH$_2$Cl$_2$). The resulting dark purple solution was stirred for 2 hr at −78° C. The reaction was quenched with CH$_3$OH, the solvent was removed in vacuo, and the resulting solid was dried overnight in vacuo. This material was dissolved in a boiling mixture of CHCl$_3$/CH$_3$OH (ca. 1:1), and the solution was heated to reflux for 1 hr. Cooling and concentration in vacuo produced a voluminous red/orange solid which was filtered and dried in vacuo to give in three crops 4-fluoro-4-demethoxydaunomycinone (2.39 g, 83%), mp 238°–241° C.

SYNTHESIS EXAMPLE 16

(±)1-Fluoro-4-demethoxydaunomycinone. To a 0° C. solution of DMSO (13 mL) and THF (13 mL) was added CH$_3$Li (3.3 mL of a 1.29 M solution). After 5 min, 4-fluoro-3-cyano-1(3H)-isobenzofuranone (0.75 g, 0.42 mmol) in DMSO (13 mL) was added, giving a yellow/brown solution. After an additional 2 min, the monoketal (1.43 g, 3.26 mmol) in THF (11.3 mL) was added rapidly, whereupon the solution turned a deep red color. The reaction mixture was allowed to stir at room temperature for 2 hr, and then the reaction was quenched by the addition of 5% HCl (40 mL). The majority of the THF was removed in vacuo, (CH$_3$)$_2$CO (100 mL) was added, and the solution was allowed to stir for 12 hr. The heterogenous solution was then cooled in an ice bath and filtered. The resulting orange/yellow solid (1.19 g, 81% crude) was used directly in the next step.

A mixture of THF (125 mL) and concentrated HCl (18 mL) was cooled to 0° C., and the above ketal (1.10 g) was added. This mixture was then stirred for 24 hr at room temperature, and the resulting homogeneous mixture was diluted with water (35 mL). The acid was neutralized by cautious addition of solid Na$_2$CO$_3$. The aqueous layer was then separated and extracted with CHCl$_3$ (2×30 mL), and the combined organic phase was concentrated in vacuo. This material was dissolved in CHCl$_3$, dried, and concentrated to give a dark residue which crystallized after addition of CH$_3$OH to give an orange powder (0.77 g, 77%, mp 157°–159° C.). This material was used directly in the next step.

To a −78° C. solution of the above material (0.77 g) in CH$_2$Cl$_2$ (160 mL) was added BCl$_3$ (19.3 mL) of a 1 M solution in CH$_2$Cl$_2$. The resulting dark purple solution was stirred for 2 hr at −78° C. The reaction was quenched with CH$_3$OH (90 mL), the solvent removed in vacuo, and the resulting solid dried overnight in vacuo. Recrystallization of this material from CHCl$_3$/CH$_3$OH gave (±)1-fluoro-4-demethoxydaunomycinone (0.48 g, 66%), mp 205°–208° C.

SYNTHESIS EXAMPLE 17

(±)1,4-Difluoro-4-demethoxydaunomycinone. To a 0° C. solution of DMSO (22.5 mL) and THF (22.5 mL) was added CH$_3$Li (6.2 mL of a 1.29 M solution). After 5 min, 4-fluoro-3-cyano-1(3H)-isobenzofuranone (1.5 g., 7.7 mmol) in DMSO (22.5 mL) was added, giving a golden brown solution. After an additional 2 min, the monoketal (2.6 g, 5.9 mmol) in THF (22.5 mL) was added rapidly, whereupon the solution turned a deep red color which took on a red/violet hue after 15 min. The reaction mixture was allowed to stir at room temperature for 2 hr, and then the reaction was quenched by the addition of 5% HCl (50 mL). The majority of the THF was removed in vacuo, (CH$_3$)$_2$CO (100 mL) was added, and the solution was allowed to stir for 12 hr. The solvents were removed in vacuo, and the resulting brown oil was dissolved in CH$_2$Cl$_2$ (500 mL) and washed with an equal volume of water (3×). Concentration and drying afforded a dark oil which was used directly in the next step.

A mixture of THF (500 mL) and 30% HCl (200 mL) was cooled to 0° C., and the above ketal was added. This mixture was then stirred for 3 days at room temperature. The reaction mixture was concentrated in vacuo to about one third of its original volume and then diluted with an equal volume of water. This mixture was then extracted with CHCl$_3$ (2×250 mL), and the CHCl$_3$ layer was washed with an equal volume of water. Standard workup and drying under vacuo for 12 hr gave a reddish brown foam which was used directly in the next step.

To a −78° C. solution of the above material (2.1 g) in CH$_2$Cl$_2$ (250 mL) was added BCl$_3$ (80 mL of a 1 M solution in CH$_2$Cl$_2$) over a period of 0.5 hr. The resulting royal purple solution was stirred for 2 hr at −70° C., and then the reaction was quenched with CH$_3$OH (375 mL). Concentration gave a dark oil which was dissolved in CHCl$_3$ and washed with water to remove residual HCl. After concentration, the mixture was redissolved in CHCl$_3$/CH$_3$OH (200:100 mL), and the solution was heated to reflux for 1 hr. Concentration to ca. 50 mL gave a beautiful red solid (0.78 g), showing an analytically pure sample by 500-MHz $^1$H NMR. This material was homogeneous by TLC but showed a wide melting-point range, 110°–125° C. The mother liquors were chromatographed on silica gel (1% CH$_2$Cl$_2$/CH$_3$OH as eluant) to afford an additional 0.78 g of slightly less pure material as judged from the 500-MHz $^1$H NMR. The total yield of material acceptable for coupling was 1.3 g (52% overall from monoketal).

SYNTHESIS EXAMPLE 18

4′-O-Acetyl-3′-N-trifluoroacetyl-4-demethoxy-4-fluorodaunomycin. To a solution of (+) 4-Demethoxy-4-fluorodaunomycinone (50.3 mg, 0.125 mmol) in dichloromethane (7 mL) was added mercuric bromide (50 mg), mercuric oxide (209 mg) and molecular sieves 4Å (0.7 g). To this prepared suspension a solution of 4-O-acetyl-2,3,6-trideoxy-3-N-trifluoroacetyl-α-L-lyxo-hexopyranopyl chloride (76.6 mg, 0.28 mmol) in dichloromethane (6 mL) was added. Reaction was stopped when thin layer chromatography (toluene:acetone/6:1) showed no aglycone in the reaction mixture. Filtration gave a red solution that was washed with 30% KI and water, then dried with MgSO$_4$ and after filtration evaporated. Crystallization from acetone:hexane gave a red solid; yield 70.6 mg: mp. 150°–152° C., $[\alpha]_D^{22}$+132° C. (c 0.05, CHCl$_3$).

SYNTHESIS EXAMPLE 19

4-Demethoxy-4-fluorodaunomycin Hydrochloride. 4′-O-Acetyl-3′-N-trifluoroacetyl-4-demethoxy-4-fluorodaunomycin (50 mg, 0.076 mmol) was dissolved in methanol and treated with sodium methoxide in methanol (0.57 mL of 0.135 M solution). The reaction was stopped by adding Dry Ice, poured into an excess of dichloromethane, and washed three times with water. The organic layer was dried with MgSO$_4$ and then filtered. Evaporation gave a red solid.

The resultant 4′-hydroxy derivative was treated witn 0.1 M sodium hydroxide (10 mL) for 25 min. Extraction with dichlormethane and dichlormethane-methanol mixture gave a red solution that was extracted with 5% hydrochloric acid solution. The solution was adjusted with base to pH 9 and washed again with dichloromethane and a dichloromethanemethanol mixture. The organic layer was dried with MgSO$_4$, filtered and evaporated to dryness. Thin layer chromatography (chloroform:methanol/2:1) showed the presence of one product. The red solid was redissolved in methanol (1 mL) and treated witn methanolic hydrochloride solution in methanol (0.5 mL, 0.28 M). Addition of an excess of ethyl ether caused the precipitation of a red solid (9.2 mg) which was filtered off and dried.

The same coupling method was used to prepare 4′-O-acetyl-3′-N-trifluoroacetyl-4-demethoxy-1,4-difluorodaunomycin with the natural 7S,9S configuration (mp 153°–154° C., $[\alpha]_D^{23}$+175° (C 0.05, CHCl$_3$) and its 7R,9R counterpart (mp 154°–155° C., $[\alpha]_D^{23}$−365° (C 0.005, CHCl$_3$)).

SYNTHESIS EXAMPLE 20

(7S,9S)-4-Demethoxy-4-fluoro-7-O-(3,4-di-O-acetyl-2,6-dideoxy-2-iodo-α-L-manno-hexopyranosyl) daunomycinone and (7R, 9R)-4-demethoxy-4-fluoro-7-0-(3,4-di-O-acetyl-2,6-dideoxy-2-iodo-α-L-manno-hexopyranosyl) daunomycinone ±4-demethoxy-4-Fluorodaunomycinone (311 mg, 0.806 mmol) was dissolved in 6 mL of acetonitrile and then 3,4-di-O-acetyl-L-rhamnal (259 mg) in oxolane (3 mL) was added. To the vigorously-stirred reaction mixture, N-iodosuccinimide (326 mg) was added and the mixture was left at room temperature overnight. After 25 hr, additional portions of 3,4-di-O-acetyl-L-rhamnal (130 mg) and N-iodosuccinimide (170 mg) were added. After 4 hr, the reaction mixture was diluted with dichloromethane and washed with 10% aqueous sodium thiosulfate and water. Drying with MgSO₄, filtration and evaporation gave a red solid. Combination of appropriate fractions from three successive chromatographic separations (toluene:acetone/9:1) gave after crystallization (dichloromethane:hexane) the (7S,9S) (108.9 mg) and (7R,9R) (120.7 mg) compounds. 7S,9S : mp 133°–135°, $[\alpha]_D^{27} -26°$ (C 0.02, CHCl₃).

Using the same procedure, the compounds (7S,9S)-4-demethoxy-1-fluoro-7-O-(3,4-di-O-acetyl-2,6-dideoxy-2-iodo-α-L-mannopyranosyl)daunomycinone [mp 128°–129°, ¹H NMR 5.73 (H-1'), 5.25 (H-7), 5.19 (H-4')]; (7S,9S)-4-demethoxy-1,4-difluoro-7-O-(3,4-di-O-acetyl-2,6-dideoxy-2-iodo-α-L-mannopyranosyl)daunomycinone [mp 142°–144°, $[\alpha]_D^{23} +23°$ (C 0.06 CHCl₃)] and its 7R, 9R analogue [mp 138°–141°, $[\alpha]_D^{23} -270°$ (C 0.05, CHCl₃)] were prepared.

SYNTHESIS EXAMPLE 21

(7S,9S)-4-Demethoxy-1-fluoro-7-O-(2,6-dideoxy-2-iodo-α-L-manno-hexopyranosyl)daunomycinone (7S,9S)-4-demethoxy-1-fluoro-7-O-(3,4-di-O-acetyl-2,6-dideoxy-2-iodo-α-L-mannopyranosyl)daunomycinone (55.8 mg, 0.077 mmol) was dissolved in methanol (200 mL) and then sodium methoxide (2.5 mL of 0.371 M solution) was added. The reaction was stopped by adding Dry Ice, diluting with dichloromethane and washing with water. The organic layer was dried with Na₂SO₄, filtered and evaporated. The obtained solid was crystallized from acetone:dichloromethane:hexane to give 28.2 mg of red precipitate (mp 132°–135°).

BIOLOGICAL EXAMPLE

Groups of mice were inoculated by intraperitoneal injection with the lymphocytic leukemia cell line P-388. On day 1, 24 hours after implantation of the tumor cells, groups of test mice were administered a single intraperitoneal dose of Compounds 1 to 4 below. For comparison, similar groups of mice were challenged with the P-388 tumor cells and given a single dose of daunomycin on day 1 following implantation of the tumor cells. The animals were observed and their survival compared with that of control animals which received the same tumor inoculation but were not treated with the drug. The survival ratio T/C, a ratio of the test Median Survival Time (MST) relative to control MST was determined. An increase in the T/C indicates an increase in the antitumor activity of the compound. If T/C is less than 100, the dosage is considered toxic. A T/C of 125 is indicative of antitumor activity.

Compound 1: 3'-deamino-4-demethoxy-3',4'-di-O-acetyl-4-fluoro-2'-iododaunomycin [4-Demethoxy-4-fluoro-7-O-(3,4-di-O-acetyl-2,6-dideoxy-2-iodo-α-L-mannopyranosyl)daunomycinone]

Compound 2: 3'-deamino-4-demethoxy-4-fluoro-2'-iododaunomycin [4-Demethoxy-4-fluoro-7-O-(2,6-dideoxy-2-iodo-α-L-mannopyranosyl) daunomycinone]

Compound 3: 4-demethoxy-4-fluorodaunomycin

Compound 4: 3'-deamino-4-demethoxy-1-fluoro-7-O-(2,6-dideoxy-2-iodo-α-L-mannopyranosyl)-daunomycinone]

Control: daunomycin.

The survival ratios are shown below:

| Dosage (mg/kg) | T/C | % Increase In Life |
|---|---|---|
| Compound 1 | | |
| 60 | 79 | — |
| 30 | 89 | — |
| 15 | 237 | 137 |
| 7.5 | 177 | 77 |
| 3.75 | 145 | 45 |
| Compound 2 | | |
| 30 | 49 | — |
| 20 | 59 | — |
| 10 | 74 | — |
| 5 | 257 | 157 |
| 2.5 | 211 | 111 |
| Compound 3 | | |
| 4 | 55 | — |
| 2 | 70 | — |
| 1 | 102 | — |
| 0.5 | 165 | 65 |
| Compound 4 | | |
| 34 | 75 | — |
| 17 | 220 | 120 |
| 8.5 | 173 | 73 |
| 4.25 | 135 | 35 |
| 2.13 | 131 | 31 |
| 1.06 | 121 | — |
| 0.531 | 115 | — |
| 0.266 | 98 | — |
| Control | | |
| 20 | 54 | — |
| 10 | 110 | — |
| 5 | 163 | 63 |

The results given in the table show that at non-toxic doses the ratio of surviving treated animals to surviving untreated animals increases significantly.

Having described the invention in detail and by reference to specific embodiments thereof, it will be apparent that numerous modifications and variations are possible without departing from the scope of the following claims.

What is claimed is:

1. A compound of the formula (I)

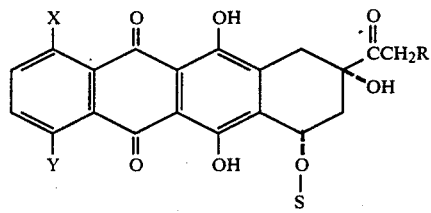

where R is hydrogen or hydroxyl, one of X and Y is fluorine and the other is hydrogen, or both X and Y are fluorine; and S is a sugar moiety; represented by the formula

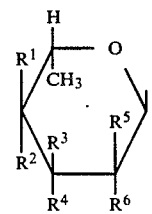

wherein one of $R^1$ and $R^2$ is hydrogen and the other is a hydroxy group or an acyloxy group containing 2 to 4 carbon atoms; one of $R^3$ and $R^4$ is hydrogen and the other is a hydrogen atom, a hydroxy group, an acyloxy group containing 2 to 4 carbon atoms or an amino group; and one of $R^5$ and $R^6$ is hydrogen and the other is fluorine, chlorine, bromine or iodine and pharmaceutically acceptable acid addition salts thereof.

2. A compound according to claim 1 wherein X is hydrogen and Y is fluorine.

3. A compound according to claim 1 wherein X is fluorine and Y is hydrogen.

4. A compound according to claim 1 wherein X and Y are fluorine.

5. A compound according to claim 1 wherein S is a 2,6-dideoxy-2-iodo-hexopyranose sugar.

6. A compound according to claim 5 wherein S is a 2,6-dideoxy-2-iodo-α-L-mannopyranosyl group.

7. A compound according to claim 6 wherein X is hydrogen and Y is fluorine.

8. A compound according to claim 6 wherein X is fluorine and Y is hydrogen.

9. A compound according to claim 6 wherein X and Y are fluorine.

* * * * *

UNITED STATES PATENT AND TRADEMARK OFFICE
CERTIFICATE OF CORRECTION

PATENT NO. : 4,663,445
DATED : May 5, 1987
INVENTOR(S) : Swenton et al.

It is certified that error appears in the above-identified patent and that said Letters Patent is hereby corrected as shown below:

Column 8, line 25, "whicn" should be --which--;

Column 9, line 9, "aoout" should be --about--;

Column 9, line 67, "witn" should be --with--.

Column 10, line 6, "or" should be --br--;

Column 12, line 13, "Thin" should be --This--;

Column 14, line 34, "(m,4)" should be --(m, 4H)--;

Column 15, line 52, "batn" should be --bath--;

Column 20, line 30, "witn" should be --with--;

Column 21, line 1, "wasned" should be --washed--; and

Column 21, line 64, after "fluoro" insert --(2'-iododaunomycin [4-Demethoxy-1-fluoro- --.

UNITED STATES PATENT AND TRADEMARK OFFICE
CERTIFICATE OF CORRECTION

PATENT NO. : 4,663,445

DATED : May 5, 1987

INVENTOR(S) : John S. Swenton et al.

It is certified that error appears in the above-identified patent and that said Letters Patent is hereby corrected as shown below:

ON THE TITLE PAGE, IN THE ABSTRACT, Formula (I) should appear as shown below:

-- 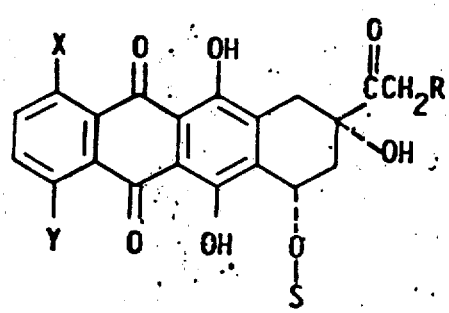 --.

Signed and Sealed this

Eighth Day of December, 1987

Attest:

DONALD J. QUIGG

Attesting Officer

Commissioner of Patents and Trademarks